United States Patent [19]

Bacon et al.

[11] Patent Number: 5,525,328

[45] Date of Patent: Jun. 11, 1996

[54] NANOPARTICULATE DIAGNOSTIC DIATRIZOXY ESTER X-RAY CONTRAST AGENTS FOR BLOOD POOL AND LYMPHATIC SYSTEM IMAGING

[75] Inventors: Edward R. Bacon, Audubon; Carl R. Illig, Phoenixville; Irennegbe K. Osifo, West Chester; Thomas S. Caulfield, Audubon, all of Pa.

[73] Assignee: NanoSystems L.L.C., Collegville, Pa.

[21] Appl. No.: 265,550

[22] Filed: Jun. 24, 1994

[51] Int. Cl.$^6$ .......................... A61K 49/04; C07C 229/60
[52] U.S. Cl. ............................................. 424/9.45; 560/47
[58] Field of Search ............................... 424/9.45; 560/47

[56] References Cited

U.S. PATENT DOCUMENTS

| | | | |
|---|---|---|---|
| 3,097,228 | 7/1963 | Larsen | 424/9.45 |
| 3,144,479 | 8/1984 | Obendorf | 424/9.45 |
| 5,318,767 | 6/1994 | Liversidge et al. | 424/4 |
| 5,318,768 | 6/1994 | Illig et al. | 424/5 |
| 5,360,604 | 11/1994 | Ruddy et al. | 424/5 |

FOREIGN PATENT DOCUMENTS

| | | |
|---|---|---|
| 241516 | 8/1959 | Australia . |
| 498482 | 8/1992 | European Pat. Off. . |
| 866184 | 5/1959 | United Kingdom . |

OTHER PUBLICATIONS

United States Patent Application Ser. No. 07/990,987 filed Dec. 16, 1992.
Siggins et al (J. Chem. Med. 8(5) 728–30 (1965).

*Primary Examiner*—Allen J. Robinson
*Assistant Examiner*—Mary C. Cebulak
*Attorney, Agent, or Firm*—Rudman & Balogh

[57] ABSTRACT

This invention relates to methods of x-ray diagnostic imaging the blood pool and/or lymph system of a mammal comprising administering a contrast effective amount of a particulate iodinated aroyloxy ester contrast agent having the structure:

wherein n is an integer from 3 to 20;

$R^1$ is H, alkyl, fluoroalkyl, cycloalkyl, aryl, aralkyl, alkoxyalkyl or acetamidoalkyl;

$R^2$, $R^3$ and $R^4$ are independently H, alkyl, fluoroalkyl, alkoxy, aryloxy, halogen, hydroxy, acylamino, acetamidoalkyl, —COO-alkyl, —COO-aryl, —COO-aralkyl, cyano, sulfonyl, carboxamido or sulfonamido;

$R^5$ is H, alkyl, fluoroalkyl, halogen, hydroxy, acylamino, acetamidoalkyl, cyano, sulfonyl, carboxamido or sulfonamido;

$R^6$ and $R^7$ are independently alkyl, cycloalkyl, aryl or aralkyl; and $R^8$ and $R^9$ are independently H or —COR$^6$.

This invention further relates to novel iodinated aroyloxy ester contrast agents having the above structure wherein n is an integer from 5 to 20, to x-ray contrast compositions comprising such agents, and to methods of x-ray diagnostic imaging utilizing such agents.

10 Claims, No Drawings

NANOPARTICULATE DIAGNOSTIC DIATRIZOXY ESTER X-RAY CONTRAST AGENTS FOR BLOOD POOL AND LYMPHATIC SYSTEM IMAGING

FIELD OF INVENTION

This invention relates to methods of x-ray diagnostic imaging the blood pool and/or lymph system of a mammal employing particulate diatrizoxy esters as a contrast agent, and to certain novel diatrizoxy esters useful as contrast agents in x-ray contrast compositions and methods of diagnostic imaging.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D. P. Swanson et al, *Pharmaceuticals in Medical Imaging*, 1990, MacMillan Publishing Company.

U.S. Pat. No. 3,097,228 describes derivatives of 2,4,6-triiodobenzoyloxyalkanoic acids having the structure

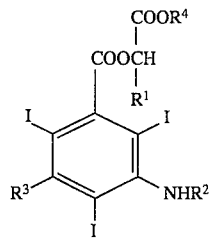

wherein $R^1$ is H or lower alkyl; $R^2$ is H or lower alkanoyl; $R^3$ is H or lower alkanoylamino and $R^4$ is lower alkyl. The agents are useful as x-ray contrast agents for visualizing the gall bladder (cholecystography) when administered orally, in the free acid form or in the form of a non-toxic salt, or intravenously, in the form of water soluble, non-toxic salt. Example 15 therein describes ethyl 2-(3,5-diacetamido-2,4,6-triiodobenzoyloxy)hexanoate, i.e.,

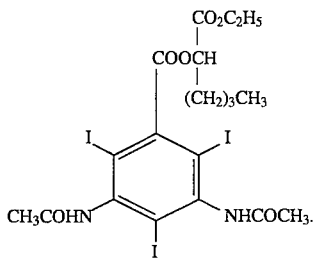

Bacon et al, commonly assigned U.S. patent application Ser. No. 07/990,987 filed Dec. 16, 1992 describes iodinated aroyloxy esters which are useful as contrast agents in x-ray imaging compositions and methods. However, all of the compounds described by Bacon et al feature an ester group linked through a $C_2$ or higher alkylene group to another ester group on an iodinated aromatic ring.

EP-A 498,482 describes nanoparticulate x-ray contrast compositions which have proven to be extremely useful in medical imaging. The compositions comprise particles of an organic x-ray contrast agent and a surface modifier adsorbed on the surface thereof and have an effective average particle size of less than 400 nm. The agents can be delivered to a specific tissue or fluid site, e.g., the blood pool, liver, spleen, kidney or lymph nodes. Example 8 therein describes a formulation comprising ethyl 2-(3,5-bis(acetylamino)-2,4,6-triiodobenzoyloxy)butyrate, i.e.,

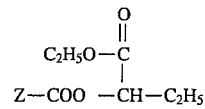

wherein (Z-)COO is the residue of diatrizoic acid.

However, it has been discovered that ethyl 2-(3,5-bis(acetylamino)-2,4,6-triiodobenzoyloxy)butyrate exhibits multiple crystal forms, i.e., polymorphs, e.g., when recrystallized from various solvents. The reasons for this behavior are not completely understood but, in any event, multiple crystal forms are disadvantageous for a variety of reasons. For example, the presence of multiple crystal forms renders scale up problematic due to the lack of reproducibility of the results obtained, including, e.g., in chemical manufacturing and in the milling process. Additionally, it has been found that nanoparticulate formulations of ethyl 2-(3,5-bis(acetylamino)-2,4,6-triiodobenzoyloxy)butyrate do not exhibit good stability during autoclaving, i.e., conventional heat sterilization.

Consequently, it would be highly desirable to provide a poorly soluble x-ray contrast agent having the advantages of ethyl 2-(3,5-bis(acetylamino)-2,4,6-triiodobenzoyloxy)butyrate but which exhibits a consistent and reproducible crystal morphology, is amenable to reproducible scale up and can be successfully heat sterilized by autoclaving.

SUMMARY OF THE INVENTION

We have discovered that certain diatrizoxy esters exhibit reproducibly consistent crystal morphology during manufacture and purification and thus are particularly amenable to reproducible scale up as particulate contrast agents for use in methods of x-ray diagnostic imaging the blood pool and lymphatic system of a mammal. In a composition of matter aspect, we have discovered and synthesized novel diatrizoxy esters which are useful as contrast agents in x-ray diagnostic imaging compositions and methods.

More specifically, in accordance with this invention, there is provided a method of medical x-ray diagnostic imaging which comprises administering to the blood pool or lymph system of a mammal a contrast-effective amount of a particulate diatrizoxy ester contrast agent having structure I:

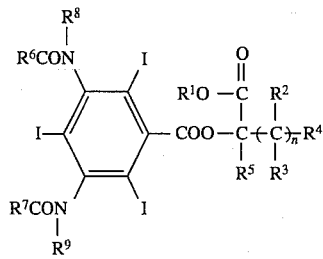

wherein n is an integer from 3 to 20;

$R^1$ is H, alkyl, fluoroalkyl, cycloalkyl, aryl, aralkyl, alkoxyalkyl or acetamidoalkyl;

$R^2$, $R^3$ and $R^4$ are independently H, alkyl, fluoroalkyl, alkoxy, aryloxy, halogen, hydroxy, acylamino, acetamidoalkyl, —COO-alkyl, —COO-aryl, —COO-aralkyl, cyano, sulfonyl, carboxamido or sulfonamido;

$R^5$ is H, alkyl, fluoroalkyl, halogen, hydroxy, acylamino, acetamidoalkyl, cyano, sulfonyl, carboxamido or sulfonamido;

$R^6$ and $R^7$ are independently alkyl, cycloalkyl, aryl or aralkyl; and $R^8$ and $R^9$ are independently H or —$COR^6$.

In another aspect, there are provided novel diatrizoxy esters having structure I above wherein n is an integer from 5 to 20. This invention further provides an x-ray contrast composition comprising such novel compounds and a method for medical x-ray diagnostic imaging which comprises administering to a mammal an effective contrast-producing amount of the above-described x-ray contrast composition.

It is an advantageous feature of this invention that methods of x-ray diagnostic imaging the blood pool and lymphatic system are provided employing an x-ray contrast composition featuring a diatrizoxy ester which exhibits a consistent crystal morphology during purification and thus is particularly amenable to reproducible scale up.

It is another advantageous feature of this invention that x-ray contrast compositions are provided for blood pool and lymphatic system imaging which exhibit improved stability during heat sterilization.

Still another advantageous feature of this invention is that novel diatrizoxy esters are provided which find particular utility as particulate x-ray contrast agents.

DESCRIPTION OF PREFERRED EMBODIMENTS

In structure I above, $R^1$ represents H; linear or branched alkyl, preferably containing from 1 to 20, more preferably from 1 to 14, and most preferably from 1 to 8 carbon atoms such as methyl, ethyl, propyl, isopropyl, butyl, pentyl, hexyl and the like; fluoroalkyl, the alkyl portion of which is as defined above and containing from 1 to (2m+1) fluorine atoms (where m=the number of carbon atoms in the alkyl group), such as trifluoromethyl; cycloalkyl, preferably containing from 3 to 8 carbon atoms such as cyclopropyl, cyclobutyl, cyclopentyl and cyclohexyl; aryl, preferably containing from 6 to 10 carbon atoms, such as phenyl and naphthyl; aralkyl, preferably containing from 7 to 12 carbon atoms, such as benzyl; alkoxyalkyl, the alkyl portions of which preferably contain from 1 to 20 carbon atoms as defined for alkyl above; or acetamidoalkyl, i.e.,

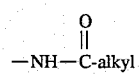

wherein alkyl is as defined above.

$R^2$, $R^3$ and $R^4$ are independently H; linear or branched alkyl, preferably containing from 1 to 20, more preferably 1 to 8 carbon atoms such as methyl, ethyl, propyl, isopropyl, butyl, pentyl, hexyl and the like; fluoroalkyl, the alkyl portion of which is as described above and containing from 1 to (2m+1) fluorine atoms (where m=the number of carbon atoms in the alkyl group), such as trifluoromethyl; alkoxy, the alkyl portion of which preferably contains from 1 to 20 carbon atoms as described above; aryloxy, the aryl portion of which preferably contains from 6 to 10 carbon atoms as described above; halogen, such as fluorine, chlorine, bromine or iodine; hydroxy; acylamino, i.e., a

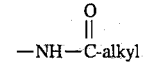

group; acetamidoalkyl, i.e.,

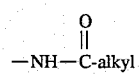

wherein alkyl is as defined above; —COO-alkyl, the alkyl portion of which is as defined above; —COO-aryl, the aryl portion of which is as defined above; —COO-aralkyl, the aralkyl portion of which is as defined above; cyano; sulfonyl; carboxamido; sulfonamido and the like.

$R^5$ represents H; alkyl as defined above; fluoroalkyl as defined above; halogen, such as fluorine, chlorine, bromine or iodine; hydroxy; acylamino, i.e., a

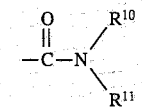

group; acetamidoalkyl, i.e.,

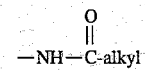

wherein alkyl is as defined above; cyano; sulfonyl; carboxamido or sulfonamido. However, reactive substituents such as halogen, hydroxy, and acylamino are not preferred on the carbon atoms closest to the ester groups. Thus, in particularly preferred embodiments, $R^5$ is H, alkyl, fluoroalkyl, acetamidoalkyl, cyano, sulfonyl, carboxamido, or sulfonamido. The reason for this is that when $R^5$ is halogen, hydroxy or acylamino, the compound tends to be more reactive and less useful as a particulate x-ray contrast agent.

$R^6$ and $R^7$ independently represent alkyl as defined above; cycloalkyl as defined above; aryl as defined above; or aralkyl as defined above.

$R^8$ and $R^9$ independently represent H or —$COR^6$, wherein $R^6$ is alkyl, cycloalkyl, aryl or aralkyl as defined above.

$R^{10}$ and $R^{11}$ are independently a substituent as defined for $R^5$ above, or $R^{10}$ and $R^{11}$, taken together with the nitrogen atom to which they are attached, represent a 4–7 membered saturated or unsaturated nitrogen containing ring such as piperidyl, piperizinyl, pyrrolidinyl, and the like.

The following compounds set forth in Table I are specific illustrative examples of preferred compounds in accordance with this invention that have been prepared. These compounds conform to structure I above wherein $R^1$ is $C_2H_5$, $R^2$, $R^3$, $R^4$ and $R^5$ are H, $R^6$ and $R^7$ are $CH_3$ and $R^8$ and $R^9$ are H.

TABLE I

| Compound | n |
| --- | --- |
| 1 | 3 |
| 2 | 4 |
| 3 | 5 |
| 4 | 6 |
| 5 | 8 |
| 6 | 10 |
| 7 | 12 |

TABLE I-continued

| Compound | n |
|---|---|
| 8 | 14 |

The compounds of this invention can be prepared by contacting the carboxylate of a diatrizoic acid with a functionalized ester having the formula

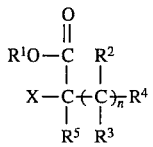

wherein X is a leaving group and n and $R^1$–$R^5$ are as defined above, in a suitable solvent. Suitable leaving groups include halogen, such as Br, I and Cl, and sulfonyloxy, such as methanesulfonyloxy and toluenesulfonyloxy. The carboxylates of iodinated aromatic acids and functionalized esters useful as the starting materials in the preparation of the compounds of this invention are known compounds and/or can be prepared by techniques known in the art. For example, suitable esters include commercially available bromoester and chloroester derivatives as exemplified below. A general reaction scheme is as follows:

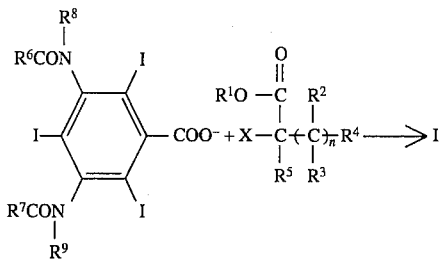

The reaction can take place at various temperatures ranging between −78° C. and 100° C. and preferably between −40° C. and 50° C. For convenience, the reaction can take place at ambient pressure, however, higher and lower pressures are contemplated.

The reaction can take place in any suitable solvent. Suitable solvents include N,N-dimethylformamide (DMF) and dimethylsulfoxide (DMSO).

The iodinated compounds can contain substituents which do not deleteriously affect the contrast-enhancing capability of the compound. For example, the alkyl, cycloalkyl, aryl, aralkyl and alkoxy groups in structure I above can be unsubstituted or substituted with various substituents which do not adversely affect the stability or efficacy of the compounds as x-ray contrast agents such as alkyl, cycloalkyl, aryl, aralkyl, alkoxy, hydroxy, acyloxy, halogen, such as chlorine, bromine and iodine, acylamino, carboalkoxy, carbamyl and the like.

When used as an x-ray contrast agent, the compound of this invention preferably comprises at least about 30%, more preferably at least 35% and most preferably at least 40% iodine by weight.

In preferred embodiments, the compounds of this invention can be formulated into particulate x-ray contrast compositions, preferably nanoparticulate x-ray contrast compositions, as described in commonly-owned EP-A 498,482. Preferred compounds exhibit a melting point of greater than 150° C. Such nanoparticulate compositions can be prepared by dispersing the compounds of the invention in a liquid dispersion medium, and wet grinding the compound in the presence of rigid grinding media and a surface modifier to form the nanoparticles. Alternatively, the surface modifier can be contacted with the compound after attrition. Preferred surface modifiers include nonionic surfactants.

In preferred embodiments, the surface modifier is a high molecular weight nonionic surfactant. Preferred surfactants include poloxamers such as Pluronic® F68 and F108, which are block copolymers of ethylene oxide and propylene oxide, poloxamines, such as Tetronic® 908 (also known as Poloxamine 908), which is a tetrafunctional block copolymer derived from sequential addition of propylene oxide and ethylene oxide to ethylenediamine, and dialkyl esters of sodium sulfosuccinic acid, such as dioctylsulfosuccinate sodium (DOSS). The concentrations of the surface modifier can vary from about 0.1–75%, preferably 1–60%, and more preferably 5–25% by weight based on the total combined weight of the contrast agent and surface modifier.

In preferred embodiments, the x-ray contrast composition in the form of surface modified nanoparticles can be associated with a cloud point modifier to further enhance stability during steam heat autoclaving, i.e., the cloud point modifier can reduce particle aggregation during heat sterilization. Preferred cloud point modifiers include nonionic cloud point modifiers, such as polyethylene glycols such as PEG 400, propylene glycol, ethanol, hydroxypropylcyclodextrin and glycerol; ionic cloud point modifiers, such as those described in U.S. Pat. No. 5,298,262 including dialkylesters of sodium sulfosuccinic acid such as the dioctylester of sodium sulfosuccinic acid (DOSS); and charged phospholipids, such as diacylphosphatidyl glycerol and dimyristoylphosphatidyl glycerol. The cloud point modifier can be present in an amount of 0.005–50%, preferably 0.01–30% and more preferably 0.05–20% by weight based on the total weight of the x-ray contrast composition.

The x-ray contrast compositions of this invention comprise the above-described compounds, preferably in the form of particles, and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast composition can comprise from about 1–99.9, preferably 2–45 and more preferably 10–30% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 20 to 450 mg of iodine per kilogram of body weight of the subject for many imaging applications. For some applications, e.g., lymphography, lower doses, e.g., 0.5–20 mg I/kg, can be effective. For blood pool imaging, the dose can range from 50 to 450 mg of iodine per kilogram of body weight and preferably from 100 to 250 mg of iodine per kilogram of body weight.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a convention manner. Alternatively, the image pattern can be observed directly on an x-ray sensitive phosphor screen-silver halide photographic film combination.

The compositions of this invention can be administered by a variety of routes depending on the type of procedure and the anatomical orientation of this tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

In addition to preferred applications, i.e., for blood pool and lymph node imaging, the x-ray contrast compositions of this invention are also expected to be useful as contrast agents for any organ or body cavity. For example, the compositions of this invention are expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

EXAMPLE 1

Preparation of Compound 3

To a stirred solution of sodium diatrizoate (150 g, 235 mmole) in dry DMF (1200 ml) was added ethyl 2-bromoheptanoate (43 g, 258.2 mmole). The solution was heated overnight at 90° C. then cooled to 60° C., whereupon the reaction mixture was poured slowly into water (20 l). The resulting white precipitate was collected by filtration and dried at 90° C. under high vacuum to give 135 g of analytically pure product, mp 250°–257° C. The mass spectral (MS) and $^1$H-NMR (300 MHz) spectral data were consistent with the desired material. Calculated for $C_{20}H_{25}I_3N_2O_6$: C 31.16, H 3.25, I 49.44; N 3.64; Found: C 30.86, H 3.13, I 49.08, N 3.60.

EXAMPLE 2

Preparation of Compound 1

To a stirred solution of sodium diatrizoate (100 g, 159.3 mmoles) in dry DMF (1200 ml) was added ethyl 2-bromovalerate (39.3 g, 187.8 mmole) and the mixture was then heated at 90° C. overnight After cooling to 60° C., the mixture was slowly poured into 20 l of water with stirring. The resulting white precipitate was collected by filtration, washed with water and dried (90° C.; high vacuum) to give 98 g of crude product. The material was recrystallized initially from DMF/$H_2O$ followed by DMF/$CH_3OH$ (1:2) to give analytically pure product, mp>270° C. The MS and $^1$H-NMR (300 MHz) spectral data were consistent with the desired product. Calculated for $C_{18}H_{21}I_3N_2O_6$: C 29.11, H 2.83, I 51.30, N 3.77; Found: C 28.88, H 2.80, I 50.94, N 3.68.

EXAMPLE 3

Preparation of Compound 2

In a manner similar to the procedures described in Examples 1 and 2 above, analytically pure compound 2, mp 263°–265° C., was prepared. The MS and $^1$H-NMR (300 MHz) spectral data were consistent with the desired structure. % Calculated/Found for $C_{19}H_{23}I_3N_2O_6$: C 30.15/30.22, H 3.04/3.00, I 50.35/50.19, N 3.70/3.66.

The aqueous solubility of Compound 2 was about 40 times lower than the solubility of ethyl 2-(3,5 -bis(acetylamino)-2,4,6-triiodobenzoyloxy)butyrate. This is a significant advantage for particulate pharmaceutical applications.

EXAMPLE 4

Preparation of Compound 4

In a manner similar to the procedures described in Examples 1 and 2 above, analytically pure Compound 4, mp 220°–222° C., was prepared. The MS and $^1$H-NMR (300 MHz) spectral data were consistent with the desired material. % Calculated/Found for $C_{21}H_{27}I_3N_2O_6$: C 32.19/32.11, H 3.44/3.36, I 48.55/48.42, N 3.57/3.55.

EXAMPLE 5

Preparation of Compound 5

In a manner similar to the procedures described in Examples 1 and 2 above, analytically pure Compound 5, mp 225°–228° C., was prepared. The MS and $^1$H-NMR (300 MHz) spectral data were consistent with the desired material. % Calculated/Found for $C_{23}H_{31}I_3N_2O_6$: C 33.98/34.00, H 3.82/3.84, I 46.87/46.83, N 3.45/3.31.

EXAMPLE 6

Preparation of Compound 6

In a manner similar to the procedures described in Examples 1 and 2 above, analytically pure Compound 6, mp 228°–231° C., was prepared. The MS and $^1$H-NMR (300 MHz) spectral data were consistent with the desired material. % Calculated/Found for $C_{25}H_{35}I_3N_2O_6$: C 35.70/35.78, H 4.17/4.22, I 45.31/45.37, N 3.33/3.25.

EXAMPLE 7

Preparation of Compound 7

In a manner similar to the procedures described in Examples 1 and 2 above, Compound 7, mp>160° C., was prepared. % Calculated/Found for $C_{27}H_{39}I_3N_2O_6$: C 37.31/40.50, H 4.49/5.11, I 43.84/38.37, N 3.22/2.77.

EXAMPLE 8

Preparation of Compound 8

In a manner similar to the procedures described in Examples 1 and 2 above, analytically pure Compound 8, mp 232°–233° C., was prepared. The MS and $^1$H-NMR (300 MHz) spectral data were consistent with the desired structure.

EXAMPLES 9–11

Preparation of Nanoparticulate Compound 2 Contrast Agents with Pluronic F68, Pluronic F108, or Tetronic T-908

Compound 2 was added to each of 3×1.5 oz brown glass bottles containing approximately 12 ml of zirconium silicate (1.1 mm dia.) beads in an amount sufficient to be 15% (w/v) of the final suspension. Bottle A contained 3% (w/v) Pluronic F-68. Bottle B contained 3% (w/v) Pluronic F108. Bottle C contained 3% (w/v) Tetronic T-908. The resulting suspensions were milled on a roller mill at approximately 150 rpm for a total of 9 days. Estimates of particle size determined at various intervals were as detailed below:

| | Examples | | |
|---|---|---|---|
| | 9 | 10 | 11 |
| Days of milling | Average Particle Size (nm) | | |
| 2 | 1939* | 158 | 162 |
| 3 | 223 | 161 | 162 |
| 7 | 157 | 158 | 156 |
| 9 | 158 | 159 | 159 |
| After 1 additional week at room temperature | 166 | 166 | 161 |
| After autoclaving at 121° C. for 20 min. | 181 | 190 | 183 |

*0.1% (w/v) DOSS was added at this point to aid in milling.

0.1% (w/v) DOSS was added to the F108 and T908 samples for autoclaving as cloud point modifiers.

These examples demonstrate the unexpected stabilization of small particles of Compound 2 with both F108 and T908 as well as their excellent stability to heat autoclaving and shelf stability. Stabilization of particle size below 200 nm after autoclaving is extremely rare.

EXAMPLES 12–13

Preparation of Nanoparticulate Compound 2 Contrast Agent with Pluronic F108 and Blood Pool Imaging 15% Compound 2 was milled with 4% Pluronic F-108 in the presence of zirconium silicate (1.1 mm dia) beads for 3 days under aseptic conditions. No additional salts or surfactants were added. The average particle size of the resulting nanoparticle suspension was 162 nm as determined by light scattering.

This sample was examined for imaging efficacy at the Center for Imaging and Pharmaceutical Research (CIPR) at the Massachusetts General Hospital in Charlestown, Mass. The sample was injected into white New Zealand rabbits at a dose of 3 ml/kg as a slow bolus injection. At times of 5, 15, 30, 60 and 120 min. post injection, the opacification of the liver, spleen, and blood pool as measured in the aorta and within the left ventricle was determined by computed tomography (CT) using a Toshiba 900S Imager CT scanner and associated software. Results from this analysis indicated that this formulation of Compound 2 had excellent blood pool opacification in excess of 30 min. followed by very good liver and very good spleen opacification for 120 min. Imaging at 24 hours post injection showed complete clearance from the blood with partial clearance from the liver and spleen.

EXAMPLES 14–15

Preparation of an Autoclavable Formulation of Nanoparticulate Compound 2 Contrast Agent with Pluronic F108 and PEG 400 and Lymphography Imaging Compound 2 was milled with zirconium silicate (1.1 mm dia) beads in the presence of Pluronic F-108 for 3 days. The final particle size was determined to be 235 nm. At this point, sterile PEG 400 was added to the suspension such that at completion, the formulation contained 15% (w/v) WIN 70146, 3% (w/v) Pluronic F-108, and 10% (w/v) PEG 400. This formulation was then autoclaved under standard conditions, i.e., 121° C. for 20 min., resulting in a final particle size of 248 nm.

This formulation was evaluated at CIPR for both blood pool and lymphographic imaging in New Zealand White Rabbits using the above-described protocol (3 ml/kg) for blood pool imaging and 2 injections (0.25 ml) per paw for lymphography. The results indicated that Compound 2 is capable of blood pool opacification to at least 30 min. and is an excellent lymphography agent affording the highest level of opacification noted to date in this indication. Scanning was carried out using a Toshiba 900S Imager CT scanner and image density was calculated from iodinated standards imaged simultaneously with the animals.

The acids of the above-described esters, i.e., wherein $R^1$ is H, can be prepared by conventional techniques known in the art. The acids and salts thereof are particularly useful as wetting agents and/or as surface modifiers in x-ray contrast compositions, particularly in nanoparticulate x-ray contrast compositions.

The invention has been described in detail with particular reference to certain preferred embodiments thereof, but it will be understood that variations and modifications can be effected within the spirit and scope of the invention.

We claim:

1. A method of medical x-ray diagnostic imaging the blood pool or lymph system of a mammal comprising administering to the mammal a contrast effective amount of a diatrizoxy ester contrast agent having the structure

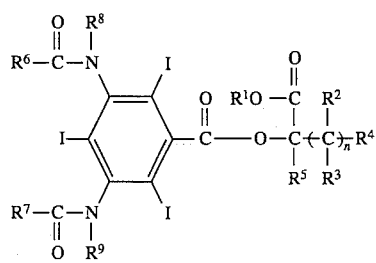

n is an integer from 3 to 20;
$R^1$ is H or alkyl;
$R^2$, $R^3$ and $R^4$ are H;
$R^5$ is H;

$R^6$ and $R^7$ are alkyl; and $R^8$ and $R^9$ are H.

2. The method of claim 1 wherein $R^1$ is $C_2H_5$.

3. The method of claim 1 wherein n is an integer from 3 to 15.

4. A compound having the structure

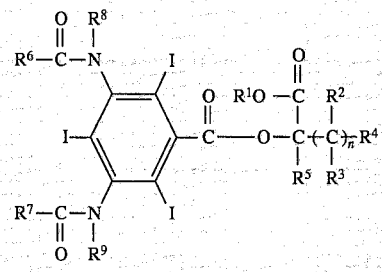

wherein n is an integer from 5 to 20;

$R^1$ is H or alkyl;

$R^2$, $R^3$ and $R^4$ are H;

$R^5$ is H;

$R^6$ and $R^7$ are alkyl; and $R^8$ and $R^9$ are H.

5. The compound of claim 4 wherein $R^1$ is $C_2H_5$.

6. The compound of claim 4 wherein n is an integer from 5 to 14.

7. An x-ray contrast composition comprising the compound of claim 4.

8. A method of claim 1, wherein the contrast agent is an ethyl 2-(3,5-bis(acetylamino)-2,4,6-triiodobenzoyloxy)alkanoate, wherein the alkyl has 3 to 14 carbon atoms.

9. A method of claim 8, wherein the contrast agent is ethyl 2-(3,5-bis(acetylamino)-2,4,6-triiodobenzoyloxy)hexanoate.

10. A compound of claim 4 being ethyl 2-(3,5-bis(acetylamino)-2,4,6-triiodobenzoyloxy)alkanoate, wherein the alkyl has 7 to 14 carbon atoms.

* * * * *